United States Patent [19]

Schreiber

[11] 4,105,758

[45] Aug. 8, 1978

[54] ORAL COMPOSITIONS CONTAINING AN ANTICALCULUS AGENT

[75] Inventor: Ronald Stanley Schreiber, Jersey City, N.J.

[73] Assignee: Colgate-Palmolive Company, New York, N.Y.

[21] Appl. No.: 754,777

[22] Filed: Dec. 27, 1976

[51] Int. Cl.$^2$ .............................................. A61K 7/16
[52] U.S. Cl. ........................................ 424/49; 424/7;
424/54; 424/56; 424/57
[58] Field of Search ................................ 424/7, 49–58

[56] References Cited

U.S. PATENT DOCUMENTS

| | | | |
|---|---|---|---|
| 1,717,723 | 6/1929 | McCall | 424/7 |
| 2,151,495 | 3/1939 | Bender | 424/7 |
| 3,584,112 | 6/1971 | Morris et al. | 424/7 |
| 3,624,219 | 11/1971 | Porlitsh | 424/7 |
| 3,903,252 | 9/1975 | Stearns | 424/7 |
| 3,997,658 | 12/1976 | Block et al. | 424/7 |

OTHER PUBLICATIONS

Merck Index 9th Ed. (1976), #231–#234, (Alizarin Dyes), #7732, (Purpurin Dye).
Sutor, British J. Urology 41:171–178, (1969), "Growth Studies of Calcium Oxalate in the Presence of Various Ions and Compounds".

*Primary Examiner*—Shep K. Rose
*Attorney, Agent, or Firm*—Robert L. Stone; Murray M. Grill; Herbert S. Sylvester

[57] ABSTRACT

Oral compositions containing an anticalculus agent selected from the group consisting of compounds having the following structural formulas:

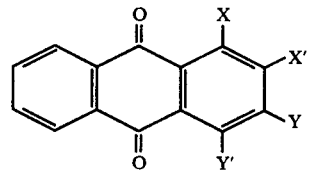

wherein X, X', Y, and Y' are selected from the group consisting of H, OH, SO$_3$Na, and CH$_2$N(CH$_2$COOH)$_2$ and additionally wherein at least two of the substituents X, X', Y, and Y' must be hydroxyls, and at least one of the further of said substituents must be OH, SO$_3$Na, or CH$_2$N (CH$_2$COOH)$_2$. The preferred anthraquinoid derivatives are Alizarin red S monohydrate, Alizarin complexone dihydrate, purpurin, and purpurin sulfonate.

9 Claims, No Drawings

ORAL COMPOSITIONS CONTAINING AN ANTICALCULUS AGENT

This invention relates to oral compositions containing an anticalculus agent.

Calculus is a hard, mineralized formation which forms on the teeth. Regular brushing prevents a rapid build-up of these deposits; but even regular brushing is not sufficient to remove all of the calculus deposits which adhere to the teeth. Calculus is formed on the teeth when crystals of calcium phosphates begin to be deposited in the pellicle and extracellular matrix of the dental plague and become sufficiently closely packed together for the aggregates to become resistant to deformation. There is no complete agreement on the route by which calcium and orthophosphate ultimately become the crystalline material called hydroxyapatite. It is generally agreed, however, that at higher saturations, that is, above the critical saturation limit, the precursor to crystalline hydroxyapatite is an amorphous or microcrystalline calcium phosphate. "Amorphous calcium phospate" although related to hydroxyapatite differs from it in atomic structure, particle morphology, and stoichiometry. The X-ray diffraction pattern of amorphous calcium phosphate shows broad peaks typical of amorphous materials, which lack the long-range atomic order characteristic of all crystalline materials, including hydroxyapatite. It is apparent therefore that agents which effectively interfere with crystalline growth of hydroxyapatite will be effective as anticalculus agents. A suggested mechanism by which the anticalculus agents of this invention inhibit calculus formation probably involves an increase of the activation energy barrier thus inhibiting the transformation of precursor amorphous calcium phosphate to hydroxyapatite.

Studies have shown that there is a good correlation between the ability of a compound to prevent hydroxyapatite crystalline growth in vitro and its ability to prevent calcification in vivo.

It is therefore an object of this invention to provide oral compositions for the treatment and prevention of calculus.

A further object of the invention is to provide oral compositions which inhibit the transformation of amorphous calcium phosphate to hydroxyapatite crystal structure normally associated with calculus.

It is another object of this invention to provide an improved method for inhibiting the formation of calculus.

These and other objects will become apparent from the following detailed descriptions.

It has now been discovered that anthraquinoid derivatives such as Alizarin red S monohydrate, Alizarin complexone dihydrate, purpurin, purpurin sulfonate and their alkali metal salts, which for the purposes of this invention are defined to include sodium, potassium, and ammonium, inhibit the transformation of amorphous calcium phosphate to hydroxyapatite and are therefore effective anticalculus agents. The above mentioned anthraquinoid derivatives have the following structural formulas;

Alizarin red S monohydrate

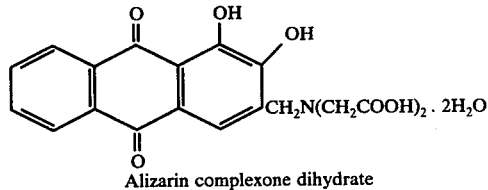
Alizarin complexone dihydrate

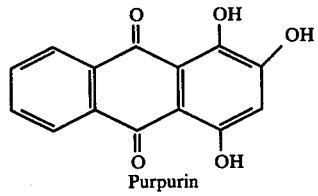
Purpurin

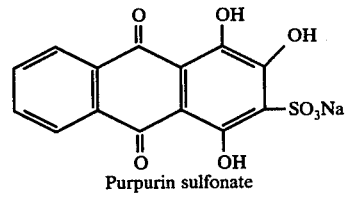
Purpurin sulfonate

More generally the anthraquinoid derivative has the formula:

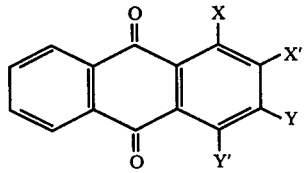

wherein X, X', Y, and Y' are selected from the group consisting of H, OH, $SO_3Na$, and $CH_2N(CH_2COOH)_2$ and additionally wherein at least two of the substituents X, X', Y, and Y' must be hydroxyls, and at least one of the further of said substituents must be OH, $SO_3Na$ or $CH_2N(CH_2COOH)_2$.

The anticalculus agent is incorporated in the oral compositions of the invention in an inhibiting amount, that is, an amount which is sufficient to prevent or diminish the formation of calculus. Generally, the toothpastes and prophylactic pastes of this invention contain from about 0.025 to about 2.0 percent by weight, preferably about 1.5 to about 2.0 percent by weight, of the anticalculus agent. The mouthwashes generally contain about 0.025 to about 1.5 percent by weight and preferably about 0.5 to about 1.0 percent by weight.

The pH of the compositions of this invention can range from 4.0 to 10. The preferred pH range is from 6 to 8. The anthraquinoid compound is preferably dissolved in the oral vehicle. The pH can be varied with acid (e.g., citric acid or benzoic acid) or base (e.g., sodium hydroxide) or buffered (as with phosphate buffers) to assist solubility. If desired, an organic solvent, e.g., ETHANOL, can also be used to assist solubility.

The dentifrice compositions of this invention contain conventional ingredients such as polishing materials, sudsing agents, binders, humectants, flavorings, etc.

Polishing materials which may be used with the anticalculus agents of this invention include hydrated alumina, dicalcium phosphate, tricalcium phosphate, insoluble sodium metaphosphate, magnesium carbonate, calcium carbonate, calcium pyrophosphate, bentonite, etc. including suitable mixtures thereof. The total amount of polishing material in the dentifrice compositions can range from 20 to 95 percent by weight of the dentifrice. Preferably, toothpastes contain from 20 to 60 percent by weight of polishing material, whereas in toothpowders the polishing material will usually be in greater proportions, such as about 70 to about 95 percent by weight. The polishing material particle size preferably ranges from $2\mu$ to $20\mu$.

In the preparation of toothpowders it is usually sufficient to admix mechanically, for example, by milling the various solid ingredients in appropriate quantities and particle sizes.

In toothpaste formulations the liquids and solids should necessarily be proportioned to form a creamy mass of desired consistency which is extrudable from an aerosol container or a collapsible tube (for example, aluminum or lead). In general, the liquids in the toothpaste will comprise chiefly water, glycerin, aqueous solutions of sorbitol, propylene glycol, polyethylene glycol 400, etc. including suitable mixtures thereof. It is advantageous usually to use a mixture of both water and a humectant or binder such as glycerin or sorbitol. The total liquid content will generally be about 20 to 75 percent by weight of the formulation. It is preferred to use also a gelling agent in toothpastes such as the natural and synthetic gums and gum-like materials, for example, Irish moss, gum tragacanth, methyl cellulose, hydroxyethyl cellulose, sodium carboxymethyl cellulose, polyvinylpyrrolidone, and starch, usually in an amount up to about 10 percent, and preferably about 0.2 to 5 percent of the formulation.

Organic surface-active agents are used in the compositions of the present invention to achieve increased prophylactic action, assist in achieving thorough and complete dispersion of the anticalculus agents throughout the oral cavity, and render the instant compositions more cosmetically acceptable. The organic surface-active material may be anionic, nonionic, ampholytic, or cationic in nature, and it is preferred to employ as the surface-active agent a detersive material which imparts to the composition detersive and foaming properties. Suitable such detergents are water-soluble salts of higher fatty acid monoglyceride monosulfates, such as the sodium salt of the monosulfated monoglyceride of hydrogenated coconut oil fatty acids, higher alkyl sulfates, such as sodium lauryl sulfate, alkyl aryl sulfonates, such as sodium dodecyl benzene sulfonate, higher alkyl sulfoacetates, higher fatty acid ester of 1,2 dihydroxy propane sulfonates, and the substantially saturated higher aliphatic acyl amides of lower aliphatic amino carboxylic acid compounds, such as those having 12 to 16 carbons in the fatty acid, alkyl, or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarcosinate compounds in dentifrice compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions.

Other particularly suitable surface-active materials include nonionic agents such as condensates of sorbitan monostearate with approximately 60 moles of ethylene oxide, condensates of ethylene oxide with propylene oxide condensates of propylene glycol (available under the trademark "Pluronics") and amophoteric agents such as quaternized imidazole derivatives which are available under the trademark "Miranol" such as Miranol $C_2M$. Cationic surface-active germicides and antibacterial compounds may also be used. Such compounds include di-isobutylphenoxyethoxyethyl dimethyl benzyl ammonium chloride, benzyl dimethyl stearyl ammonium chloride, tertiary amines, having one fatty alkyl group (of from 12 to 18 carbon atoms) and two (poly)oxyethylene groups attached to the nitrogen (typically containing a total of from about 2 to 50 ethenoxy groups per molecule) and salts thereof with acids, and compounds of the structure

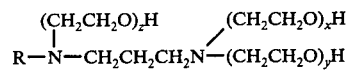

where R is a fatty alkyl group containing from about 12 to 18 carbon atoms, and $x$, $y$, and $z$ total 3 or higher, as well as salts thereof with mineral or organic acids. It is preferred to use from about 0.05 to 5 percent by weight of the foregoing surface-active materials in the instant oral preparations.

In accordance with certain additional aspects of this invention, cationic antibacterial agents are included in the compositions of the present invention. Such agents include:

$N^1$-(4-chlorobenzyl)-$N^5$(2,4-dichlorobenzyl)biguanide
p-chlorophenyl biguanide
4-chlorobenzhydryl biguanide;
4-chlorobenzhydrylguanylurea;
N-3-lauroxypropyl-$N^5$-p-chlorobenzylbiguanide;
1,6-di-p-chlorophenylbiguanidohexane;
1-(lauryldimethylammonium)-8-(p-chlorobenzyldimethylammonium octane dichloride;
5-6-dichloro-2-guanidinobenzimidazole;
$N^1$-p-chlorophenyl-$N^5$-laurylbiguanide;
5-amino-1,3-bis(2-ethylhexyl)-5-methylhexahydropyrimidine;

and their nontoxic acid addition salts, particularly the fluorides and the dihydrogen fluorides. 1,6-di-(p-chlorophenylbiguanidohexane) is particularly preferred. These agents may be used in amounts ranging from about 0.01 to 5 percent and preferably about 0.05 to 1.0 percent by weight of the dentifrice.

Any suitable flavoring or sweetening material may be employed in formulating a flavor for the compositions of the present invention. Examples of suitable flavoring constituents include the flavoring oils, for examples, oils of spearmint, peppermint, wintergreen, sassafras, clove, sage, eucalyptus, marjoram, cinnamon, lemon, and orange, as well as methyl salicylate. Suitable sweetening agents include sucrose, lactose, maltose, sorbitol, sodium cyclamate, perillartine, and saccharine. Suitably, flavor and sweetening agent together comprise from about 0.01 to 5 percent by weight or more of the compositions of the instant invention.

The compositions of the present invention desirably may also contain a fluorine-containing compounds having a beneficial effect on the care and hygiene of the oral cavity, for example, diminution of enamel solubility in acid and protection of the teeth against decay. Examples thereof include sodium fluoride, sodium monofluorophosphate, stannous fluoride, potassium fluoride, potassium stannous fluoride, ($SnF_2$-KF) and stannous chlorofluoride. These materials, which dissociate or release fluorine-containing ions, suitably may be present in an effective but nontoxic amount, usually within the range of about 0.01 to 1 percent by weight of the water-soluble fluorine content thereof. Sodium fluoride, sodium monofluorophosphate, and stannous fluoride are particularly preferred, as well as mixtures thereof.

Various other materials may be incorporated in the oral preparations of this invention. Examples thereof are coloring or whitening agents, preservatives, silicones, chlorophyll compounds, ammoniated materials such as urea, diammonium phosphate, and mixtures thereof, and other constituents. These adjuvants are incorporated in the instant compositions in amounts which do not substantially adversely affect the properties and characteristics desired and are selected and used in proper amounts depending upon the particular type of preparation involved.

In the laboratory the following tests were made to determine the effectiveness of the anticalculus agents of this invention.

In vitro Determination of Crystal Growth Inhibitors

Standard solutions of 0.1M calcium chloride and 0.1M sodium dihydrogen phosphate were prepared. 1 ml. phosphate solution was placed in a test vessel with 21, 22, or 23 ml. of distilled water. For the water control 23 ml. of water were added; for the alcohol control 22 ml. of water and 1 ml. of ethanol were added; for the determination of crystal growth inhibitors 21 ml. of water and 2 ml. of the test compound, or 22 ml. of water and 1 ml. of the test compound were added and the pH adjusted to 7.4 (NaOH was used). To these systems 1 ml. of calcium solution was added and the pH was adjusted to 7.4. The consumption of NaOH was recorded automatically by a pH-stat, and the tests were run at about 25° C (room temperature). The reaction was allowed to continue until a second rapid consumption of base was essentially complete or until it was evident that there was total blockage of crystal growth of hydroxyapatite and no significant second up take of base would occur. A delay in the time of the second rapid consumption of base versus a control or a total absence of the second rapid consumption indicates an interference in the normal crystalline growth of hydroxyapatite. The delay times for the anticalculus compounds and the controls are found in the following Table:

| DELAY TIMES OF ANTICALCULUS COMPOUNDS | | | |
|---|---|---|---|
| Compound | Concentration (gm./100ml.) ($H_2O$ or ETOH) | Control Delay Time (minutes) | Delay Time (minutes) |
| Alizarin red S Monohydrate | 0.0342(water) | 27 | 59 |
| Purpurin | 0.0256(ETOH) | 15 | 54(21 ml $H_2O$ 2 ml test) |
| Purpurin Sulfonate | 0.0350(ETOH) | 15 | 25(22 ml $H_2O$ 1 ml test) |

To test the anticalculus agents in compositions a placebo mouthwash and dentifrice were prepared. The placebo mouthwash contained the following:

| | Percent |
|---|---|
| Ethanol | 15.000 |
| Pluronics | 3.000 |
| Glycerine | 10.000 |
| Saccharin | 0.035 |
| Flavor F 193-34 | 0.220 |
| Water | 71.745 |

The pH of the mouth rinse was adjusted to 7.0. One control test run contained:

| | |
|---|---|
| 1 ml. $NaH_2PO_4$ 22 ml. distilled water | 2 ml. placebo rinse 1 ml. distilled water |
| 1 ml. water/rinse mix 1 ml. $CaCl_2$ | (mixed 15 minutes with magnetic stirrer) |

The active test run contained:

| | |
|---|---|
| 1 ml. $NaH_2PO_4$ 22 ml. distilled water | 2 ml. placebo rinse 1 ml. 0.003M Alizarin red S |
| 1 ml. compound/rinse mix 1 ml. $CaCl_2$ | monohydrate (mixed 15 minutes with magnetic stirrer) |

The control run produced a delay time of 22 minutes whereas the run containing Alizarin red S monohydrate produced a delay time of 55 minutes.

Another active test run contained:

| | |
|---|---|
| 1 ml. $NaH_2PO_4$ | 2 ml. 0.001M purpurin sulfonate in ETOH |
| 21 ml. distilled water 2 ml. compound/rinse mix 1 ml. $CaCl_2$ | 1 ml. placebo rinse (mixed 15 minutes with magnetic stirrer) |

The control alcohol run produced a delay time of 16 minutes whereas the run containing purpurin sulfonate produced a delay time of 40 minutes.

Another active run contained:

| | |
|---|---|
| 1 ml. $NaH_2PO_4$ 21 ml. distilled water | 2 ml. 0.001M purpurin in ETOH 1 ml. placebo rinse |
| 2 ml. compound/rinse mix 1 ml. $CaCl_2$ | (mixed 15 minutes with magnetic stirrer) |

The control alcohol run produced a delay time of 17 minutes whereas the run containing purpurin produced a delay time of 32 minutes.

These control runs contained no active agent, 21 ml of distilled water, and 2 ml of a 2:1 mix of water and placebo for the comparison with Alizarin red S and 2 ml of a 2:1 mix of ETOH and placebo for each of the comparisons with purpurin sulfonate and with purpurin. The controls were otherwise unchanged.

The placebo toothpaste contained the following:

| | Percent |
|---|---|
| Glycerin | 22.0 |
| Hydroxyethyl cellulose | 1.0 |
| Sodium saccharin | 0.2 |
| Polyoxyethylene monoisostearate | 1.0 |
| Flavor | 1.0 |
| Sweetener | 0.1 |
| Hydrated alumina | 42.0 |

-continued

| | Percent |
|---|---|
| Calcined aluminum | 10.0 |
| Water | 22.7 |

The control test toothpaste contained:

| | |
|---|---|
| 1 ml. NaH$_2$PO$_4$ | 2 gm. placebo toothpaste |
| 22 ml. distilled water | 4 ml. distilled water |
| 1 ml. water/toothpaste mix | (mixed 15 minutes with a magnetic stirrer; |
| 1 ml. CaCl$_2$ | centrifuge 5 minutes and remove 1 ml. supernatant) |

The active test toothpaste contained:

| | |
|---|---|
| 1 ml. NaH$_2$PO$_4$ | 2 gm. placebo toothpaste |
| | 4 ml. distilled water |
| 22 ml. distilled water | 0.00379 gm. Alizarin complexone |
| 1 ml. compound/toothpaste mix | dihydrate (mixed 15 minutes with a magnetic stirrer; |
| 1 ml. CaCl$_2$ | centrifuge 5 minutes and remove 1 ml. supernatant) |

The control toothpaste produced a delay time of 30 minutes whereas the rinse containing Alizarin complexone dihydrate produced a delay time that was stopped at 1 hour 52 minutes.

The preceding compositions are illustrative of the practice of the invention. It is to be understood, however, that various changes and modifications may be made in the materials utilized, the proportions of the materials, and the methods of formulation without departing from the spirit of the invention or the scope of the appended claims.

What is claimed is:

1. An oral preparation comprising a humectant vehicle containing a dental-calculus inhibiting amount of an anticalculus agent selected from the group consisting of compounds having the structural formula:

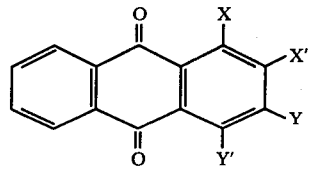

wherein X, X', Y, and Y' are selected from the group consisting of H, OH, SO$_3$Na, and CH$_2$N(CH$_2$COOH)$_2$ and wherein at least two of the substituents X, X', Y, and Y' are OH, and at least one of the further substituents are selected from the group consisting of OH, SO$_3$Na, and CH$_2$N(CH$_2$COOH)$_2$.

2. The oral preparation according to claim 1 in which the anticalculus agent is selected from the group consisting of Alizarin Red S monohydrate. Alizarin complexone dihydrate, purpurin, and purpurin sulfonate.

3. The oral preparation according to claim 1 in which said vehicle contains a dental polishing material and the anticalculus agent is present in an amount of from about 0.025 to 2.0 percent by weight.

4. An oral preparation according to claim 1 in which said vehicle is an aqueous-alcoholic vehicle and said anticalculus agent is present in amount of from about 0.025 to 1.5 percent by weight.

5. The oral preparation according to claim 4 in which the anticalculus agent is selected from the group consisting of Alizarin red S monohydrate, Alizarin complexone dihydrate, purpurin, and purpurin sulfonate.

6. A method for inhibiting the formation of dental calculus which comprises applying to teeth an oral composition containing a calculus inhibiting amount of a member selected from the group consisting of Alizarin red S monohydrate, Alizarin complexone dihydrate, purpurin, and purpurin sulfonate in a humectant vehicle.

7. An oral preparation comprising a humectant toothpaste vehicle containing an alumina abrasive and about 0.1 to 2.0 percent by weight of Alizarin complexone dihydrate.

8. A method in accordance with claim 6 wherein the said vehicle contains 20 to 95% dental polishing agent and the anticalculus agent constitutes about 0.025 to 2.0% by weight.

9. A method in accordance with claim 6, wherein said vehicle is an aqueous-alcoholic vehicle and the anticalculus agent constitutes about 0.025 to 1.5% by weight.

* * * * *